(12) United States Patent
Ohtsu et al.

(10) Patent No.: US 7,586,085 B2
(45) Date of Patent: Sep. 8, 2009

(54) PHOTO-DETECTION DEVICE AND METHOD (75) Inventors: Motoichi Ohtsu, Tokyo (JP); Motonobu Kourogi, Kanagawa (JP); Shuji Mononobe, Kanagawa (JP); Takashi Yatsui, Kanagawa (JP); Koji Yamamoto, Kanagawa (JP); Toshiyuki Inokuchi, Tokyo (JP); Masato Takada, Tokyo (JP)

(73) Assignees: Kanagawa Academy of Science and Technology, Kawasaki-shi (JP); Hoden Seimitsu Kakokenkyusho Co., Ltd., Atsugi-shi (JP); Ricoh Company, Ltd., Tokyo (JP)

( * ) Notice: Subject to any disclaimer, the term of this patent is extended or adjusted under 35 U.S.C. 154(b) by 310 days.

(21) Appl. No.: 10/563,626

(22) PCT Filed: Jul. 8, 2004

(86) PCT No.: PCT/JP2004/009748

§ 371 (c)(1),
(2), (4) Date: Sep. 11, 2006

(87) PCT Pub. No.: WO2005/003737

PCT Pub. Date: Jan. 13, 2005

(65) Prior Publication Data

US 2007/0018082 A1 Jan. 25, 2007

(30) Foreign Application Priority Data

Jul. 8, 2003 (JP) .............................. 2003-193680

(51) Int. Cl.
H01J 3/14 (2006.01)
H01J 37/00 (2006.01)

(52) U.S. Cl. .............................. 250/227.3; 250/227.11; 250/234; 385/12; 385/43; 385/123; 356/73

(58) Field of Classification Search ................. 356/601, 356/72–73; 250/234, 235, 216, 227.11, 227.3; 385/123, 128, 129, 43, 31
See application file for complete search history.

(56) References Cited

U.S. PATENT DOCUMENTS 5,361,314 A * 11/1994 Kopelman et al. ............ 385/12

(Continued)

FOREIGN PATENT DOCUMENTS

JP 7-260808 10/1995

(Continued)

Primary Examiner—Sang Nguyen
(74) Attorney, Agent, or Firm—Oblon, Spivak, McClelland, Maier & Neustadt, P.C.

(57) ABSTRACT

The broad range measurement exploiting the usual propagated light and the high resolution measurement mode exploiting near-field light are to be accomplished with a sole as-assembled optical probe. To this end, light radiated through an optical probe 13 having a light shielding coating layer 33 formed for defining a light radiating aperture D or light radiated at a core 31 of the optical probe 13 is propagated, as the optical probe 13 is moved in a direction towards and away from a surface for measurement 2a. The core of the optical probe is coated with a light shielding coating layer 33. In this manner, a spot of propagated light propagated through the core 31 or a spot of near-field light seeping from the light radiating aperture D is formed on the surface for measurement 2a, and light derived from the spot of light is detected.

19 Claims, 6 Drawing Sheets

U.S. PATENT DOCUMENTS

| | | | |
|---|---|---|---|
| 5,363,463 A * | 11/1994 | Kleinerman | 385/123 |
| 5,664,036 A * | 9/1997 | Islam | 385/31 |
| 5,928,525 A * | 7/1999 | Ohtsu et al. | 216/24 |
| 6,064,060 A * | 5/2000 | Konada | 250/234 |
| 6,118,521 A * | 9/2000 | Jung et al. | 356/73 |
| 6,236,783 B1 * | 5/2001 | Mononobe et al. | 385/43 |
| 6,370,306 B1 * | 4/2002 | Sato et al. | 385/129 |
| 7,247,012 B2 * | 7/2007 | Anand et al. | 425/131.1 |
| 7,274,012 B2 * | 9/2007 | Itoh et al. | 250/234 |
| 2003/0085351 A1 * | 5/2003 | Nakajima et al. | 250/306 |

FOREIGN PATENT DOCUMENTS

| | | |
|---|---|---|
| JP | 10-293133 | 11/1998 |
| JP | 2000-67462 | 3/2000 |
| JP | 2000-97839 | 4/2000 |

\* cited by examiner

PHOTO-DETECTION DEVICE AND METHOD

TECHNICAL FIELD

This invention relates to an apparatus and a method for light detection applicable to, for example, a light microscope usable for measuring physical properties by exploiting near-field light generated in a near-field region.

The present application claims priority rights based on the JP Patent Application 2003-193680, filed in Japan on Jul. 8, 2003, and which is to be incorporated in its entirety by reference herein.

BACKGROUND ART

Recently, a device of a miniaturized structure of a nanometric size, exemplified by a single molecule optical memory or a single electron device, is being put to practical use, on the basis of development of the fine processing technology. The near-field optical microscope, having a resolution of a nanometric size, is attracting attention as a technique indispensable for development and evaluation of such device. This near-field optical microscope detects the intensity, wavelength or polarization, for example, of emitted or propagated light from a specimen to help to give information on physical properties of the specimen from the emitted or propagated light from the specimen.

The near-field optical microscope includes an optical probe including in turn a core formed of optical fiber and a clad formed about the core. The core has a sharpened protrusion at its distal end, coated with metal, such as Au or Ag. With the near-field optical microscope, it is possible to obtain an optical image with a resolution beyond the wavelength of light. That is, with use of this near-field optical microscope, it is possible not only to measure physical properties of a minute region of a specimen with resolution of the order of nanometers, but also to perform memory operations, such as read or write, and even optical machining. The above optical probe, used in this near-field optical microscope, has already been disclosed.

In measuring the physical properties in the minute region of the specimen, with this near-field optical microscope, the evanescent light, localized in a surface region on the specimen, smaller than the light wavelength, is detected, in order to measure the shape of the specimen. This evanescent light, generated on irradiation of the specimen with light under total reflection conditions, is scattered by the above optical probe so as to be thereby converted into scattered light. The scattered light, obtained in this manner, is guided to the core of the optical fiber, through the protrusion of the optical probe, so as to be detected by a photodetector provided at the opposite side light radiating end of the optical fiber. Thus, it is possible with this near-field optical microscope to effect both scattering and detection by the optical probe including the protrusion.

Meanwhile, the above-described near-field optical microscope, enabling measurement with a high resolution, has a demerit that the measurement range is as narrow as tens of μm. On the other hand a laser microscope, employing usual propagated light, providing for broad range measurement, is inferior in resolution to e.g. a near-field optical microscope.

Moreover, the resolution of a near-field optical microscope is limited by the diameter of the aperture of the optical probe used, so that, in case the physical properties are measured as the resolution is changed, it is necessary that an optical probe for low resolution, different in the aperture diameter, be separately mounted on the near-field optical microscope. Thus, in switching to measurement with high resolution, exploiting near-field light, it is necessary to exchange the optical probes to be in use, as a routine operation, so that the user cannot be relieved of excess load. There also arises a problem that this leads to deviated positions of the optical probe, already adjusted, relative to the minute area, the physical properties of which are desired to be measured.

DISCLOSURE OF THE INVENTION

In view of the above depicted status of the art, it is an object of the present invention to provide an apparatus and a method whereby both broad range measurement employing usual propagated light and high resolution measurement employing near-field light may be achieved using an as-assembled sole optical probe.

For accomplishing the above object, the present invention provides a light detecting apparatus in which the distal end of an optical fiber probe faces a surface for measurement, a spot of light from the optical fiber probe is formed on the surface for measurement, and light from the surface for measurement is detected by the optical fiber probe, in which the apparatus has a broad range measurement mode exploiting the light propagated through a core of the optical fiber probe and a high resolution measurement mode exploiting near-field light seeping from the core of the optical fiber probe.

For accomplishing the above object, the present invention also provides a light detecting method in which a distal end of an optical fiber probe faces a surface for measurement, a spot of light from the optical fiber probe is formed on the surface for measurement, and light from the surface for measurement is detected by the optical fiber probe, in which the method has a broad range measurement mode exploiting the light propagated through a core of the optical fiber probe and a high resolution measurement mode exploiting near-field light seeping from the core of the optical fiber probe.

BEST MODE FOR CARRYING OUT THE INVENTION

Referring to the drawings, preferred embodiments of the present invention will be explained in detail.

Figure 1:
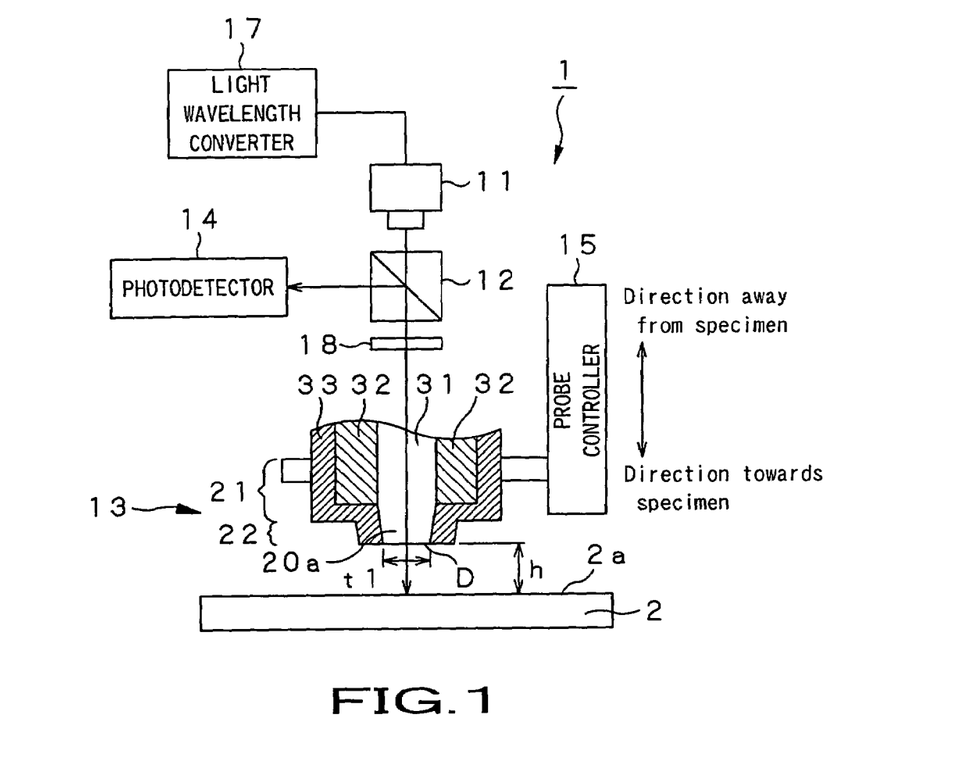
FIG. 1 is a schematic view showing an illustrative structure of a light detecting apparatus according to an embodiment of the present invention.

The present invention is applied to a light detecting apparatus 1 shown for example in FIG. 1. This light detecting apparatus 1 includes a light source 11, for radiating light, a polarization beam splitter 12, arranged in a path of light radiated from the light source 11, a quarter wave plate 18, arranged on a path of light transmitted through the polarization beam splitter 12, an optical probe 13 for collecting light transmitted through the quarter wave plate 18 for illuminating the light on a surface for measurement 2a of a specimen 2, and a photodetector 14 for detecting return light from the surface for measurement 2a. The light source 11 is the one used for radiating light used e.g. in a near-field optical microscope configured for measuring physical properties in a small-sized region of a specimen.

The light source 11 oscillates light based on the driving power supplied from a power supply device, not shown, and is connected to a light wavelength converter 17 adapted for switching the wavelengths of radiated light responsive to respective measurement modes which will be explained subsequently.

The polarization beam splitter 12 allows the light radiated from the light source 11 to be transmitted therethrough to route the light to the surface for measurement 2a, while reflecting the return light from the surface for measurement 2a to guide the return light to the photodetector 14. The light transmitted through the polarization beam splitter 12 is caused to fall on the quarter wave plate 18.

Meanwhile, a beam splitter of the ordinary sort may also be used in place of the polarization beam splitter 12.

The quarter wave plate 18 gives the light, transmitted therethrough, a phase difference equal to □/2. The linear polarized light, radiated from the light source 11, is transmitted through the quarter wave plate 18 so as to be thereby turned into circularly polarized light, which is directly incident on a core 31 of the optical probe. The circularly polarized light, returned after reflection from the surface for measurement 2a, and transmitted through this quarter wave plate 18, is turned into linearly polarized light, having the direction of light polarization different from that of light emanating from the light source, and hence is reflected by the polarization beam splitter 12.

The optical probe 13 includes a light guide section 21 and a protuberant section 22. The light guide section 21 is formed by an optical fiber and comprised of a core 31 about which is provided a clad 32. The core 31 and the clad 32 are each formed of $SiO_2$ based glass added by, for example, F, $GeO_2$ or $B_2O_3$ and are thereby adjusted in texture so that the clad 32 will be lower in the refractive index than the core 31.

The protuberant section 22 includes a core 20a protruded from the clad at one end of the light guide section 21. This protruded core 20a is tapered towards the distal end of the optical probe 13, as shown in FIG. 1. A light radiating aperture D is formed centrally of the protruded core 20a. The light radiating aperture D has a diameter t determined in dependence upon the propagation mode, transmittance/refractive index and further upon the light efficiency.

This optical probe 13 also radiates the light propagated through the core 31 via light radiating aperture D. The light propagated through the core 31 is referred to below as propagated light. When a distance h is larger than □/4, where the □ is the wavelength of light radiated from the light source, the propagated light, thus radiated, is illuminated on the surface for measurement 2a. In case the surface for measurement 2a is measured using this propagated light, the measurement is referred below as broad range measurement.

In addition, the near-field light, as evanescent wave, seeps out from the end face of the radiating aperture D of the optical probe 13. The so seeping near-field light is illuminated on the surface for measurement 2a in case the distance h (the distance between the light radiating aperture D and the surface for measurement 2a) is not larger than □/4, where the □ is the wavelength of light radiated from the light source. In case the surface for measurement 2a is measured using this near-field light, the measurement is termed a high resolution measurement.

It should be noted that classification between the broad range measurement and the high resolution measurement may also be based on, for example, the relationship of the distance h with respect to the light radiating aperture D, instead of on the above-described inter-node interference relationship of the distance h with respect to the wavelength of light. Specifically, the measurement in case the distance h is not larger than the light radiating aperture D and that in case the distance h is larger than the light radiating aperture D may be the high resolution measurement and the broad range measurement, respectively.

Meanwhile, a light shielding coating layer 33 is formed on the surface of an optical fiber, constituting the optical probe 13, so that the light radiating aperture D will be formed centrally of the protruded core 20a. This light shielding coating layer 33 is formed by a thin film of a light shielding material, such as Au, Ag or Al. In particular, the thin film may be formed of Au, exhibiting chemical stability, for possibly suppressing oxidation otherwise caused by contact with outside air.

The optical probe 13 is further mounted to a probe controller 15. This probe controller 15 is formed by e.g. a biaxial actuator adapted for causing movement of the optical probe 13 in a direction towards and away from the surface for measurement 2a or for sweeping the optical probe in a horizontal direction. Meanwhile, the surface for measurement 2a may be moved in a direction towards and away from the optical probe 13, in place of causing movement of the optical probe 13 in a direction towards and away from the surface for measurement 2a.

The photodetector 14 receives the return light from the surface for measurement 2a and processes the so received return light with photoelectric conversion to generate luminance signals. An image then is generated on the basis of the luminance signals, generated by this photodetector 14, and is demonstrated on a display, not shown. The user then is able to measure and observe details of the surface for measurement 2a, based on the image demonstrated on the display, not shown.

In the light detecting apparatus 1, described above, the light of the wavelength □, radiated from the light source 11, is transmitted through the polarization beam splitter 12, and has polarized light components thereof controlled by the quarter wave plate 18, so as to be then incident on the optical probe 13. The light incident on the optical probe 13 is then directly propagated through the core 31.

Figure 2A:
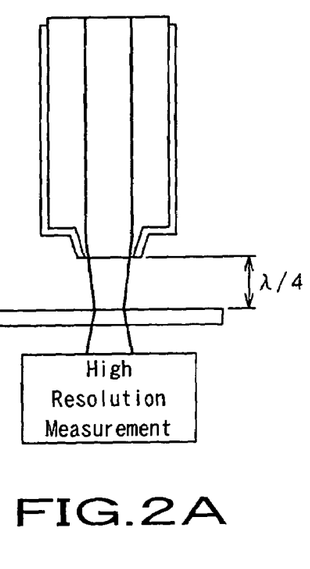
FIGS. 2A and 2B are schematic views for illustrating high resolution measurement and broad range measurement, respectively.

During the high resolution measurement, the probe controller 15 causes movement of the optical probe 13 in a direction approaching to the surface for measurement, up to an area where the distance h is not larger than the wavelength □/4, as shown for example in FIG. 2A. This area is referred to below as a near-field region. The result is that the near-field light, seeping from the end face of the light radiating aperture D, is illuminated on the surface for measurement 2a to form a small-sized spot with the near-field light.

Figure 2B:
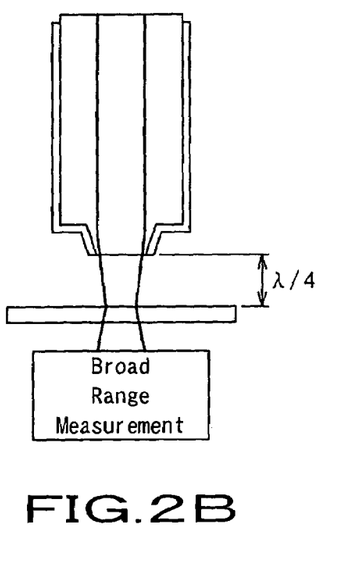

During the broad range measurement, on the other hand, the probe controller 15 causes movement of the optical probe 13 in a direction away from the surface for measurement, up to a region where the distance h is larger than the wavelength λ/4, as shown for example in FIG. 2B. This allows the light, propagated through the core, to be directly radiated and illuminated on the surface for measurement 2a, so that a spot of a larger size is formed by the propagated light.

By the way, the propagated light or the near-field light, reflected by the surface for measurement 2a, is again incident via light radiating aperture D on the optical probe 13 and propagated through the core 31. The propagated light or the near-field light, radiated from the core 31, is reflected by the polarization beam splitter 12 and guided to the photodetector 14. The propagated light or the near-field light, thus guided to the photodetector 14, is converted into luminance signals, for enabling the measurement by the user.

The user may view or recognize an image, derived from the spot by the propagated light, or an image derived from the spot by the near-field light, formed on the surface for measurement 2a, on a display, not shown.

That is, with the light detecting apparatus 1, embodying the present invention, the spot derived from the propagated light or that derived from the near-by field may be selectively switched and formed on the surface for measurement 2a, by causing movement of the as-assembled sole optical probe 13, in a direction towards and away from the surface for measurement 2a, so that both the broad range measurement exploiting the propagated light and the high resolution measurement exploiting the near-field light may be realized with the sole optical probe 13.

Thus, there is no necessity of separately arranging an optical probe, used solely for broad-range measurement, in a measurement system capable of achieving high resolution measurement, exploiting the near-field light, with the result that the apparatus may be reduced in size, and hence the production cost may appreciably be reduced.

Since the optical probes in use need not be exchanged when switching the measurement mode from the broad range measurement to the high resolution measurement, the user may be relieved of excessive labor in doing the exchange operations.

With the present light detecting apparatus 1, the optical probe 13 may initially be moved in a direction away from the surface for measurement 2a to illuminate the propagated light on the surface for measurement 2a to carry out broad-range measurement, and subsequently moved in a direction towards the surface for measurement 2a to illuminate the near-field light thereon to carry out high resolution measurement.

In this manner, the entire surface of the specimen surface may be observed under the same principle as that for a routine light microscope, by scanning the specimen surface over a wide range, at the time of the broad range measurement, for specifying a small area, the physical properties of which are to be measured in detail. The optical probe 13 may then be swept in the horizontal direction as far as the so specified area and, after achieving the position registration, the high resolution measurement may be carried out using the aforementioned near-field light.

In particular, since the optical probe 13 may be kept at a fixed height from the surface for measurement 2a, in case of measuring the physical properties by the propagated light, during the broad range measurement, it becomes unnecessary to perform control for causing movement of the optical probe in a direction towards and away from the surface for measurement, in the course of the broad range measurement, and hence the measurement at a higher speed is feasible. In addition, the constraint as to the control bandwidth in the direction towards and away from the surface for measurement may be relieved. Since the range of measurement per measurement point may be broader and of lower resolution than in high resolution measurement employing near-field light, the range of measurement may be broader for the same number of measurement points.

In particular, with the light detecting apparatus 1, in which two spots, one for the propagate light and one for the near-field light, may be formed on the surface for measurement 2a with use of the sole optical probe 13, the exchange operation for the optical probe may be dispensed with, so that there is no risk that the position of the optical probe 13, already adjusted with respect to the small-sized area during the broad range measurement, should become offset for the high resolution measurement.

In particular, an image for high resolution measurement with a narrow field of view and an image for broad range measurement with a broad field of view may be acquired, without exchanging the optical probes, by exploiting the fact that the two spots, formed on the surface for measurement 2a, differ in size from each other.

Meanwhile, with the light detecting apparatus 1, embodying the present invention, a variety of measurement operations may be executed by exploiting the fact that the profile of light for different values of the distance d from the light radiating aperture D differs with the wavelengths, and by further controlling the wavelength of light radiated from the light source 11.

Figure 3:
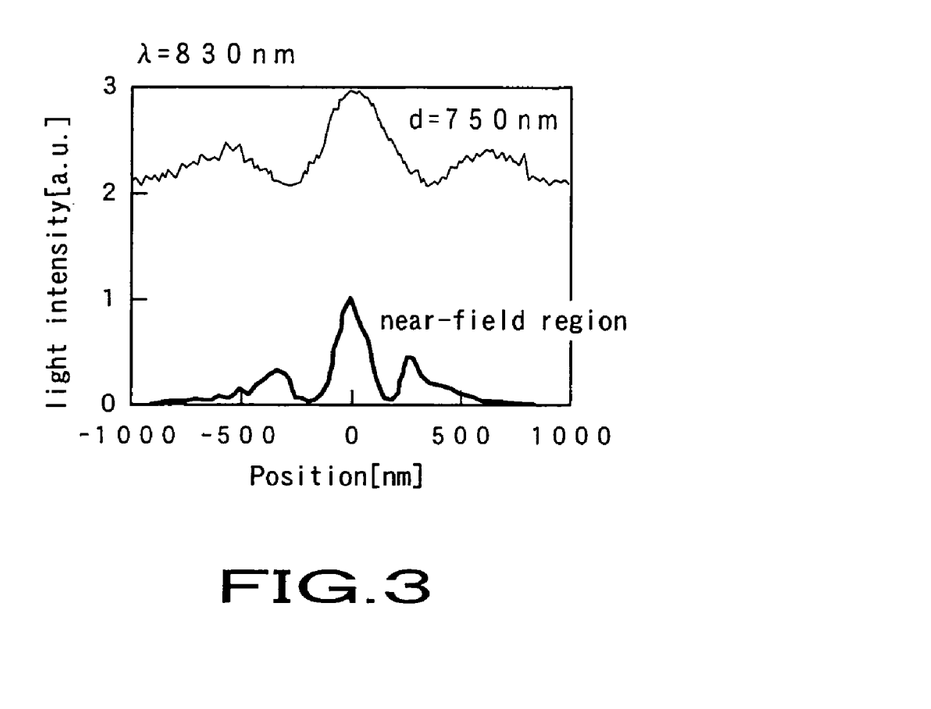
FIG. 3 is a graph showing the profile of light radiated from a light source in case the light has a wavelength ☐ of 830 nm.

FIG. 3 shows profiles of light in case the wavelength λ of light radiated from the light source 11 is 830 nm. As may be seen from FIG. 3, the profile of light at the distance d (=750 nm) from the light radiating aperture D has been enlarged to 1.5 times the spot diameter in the near-field region.

Figure 4:
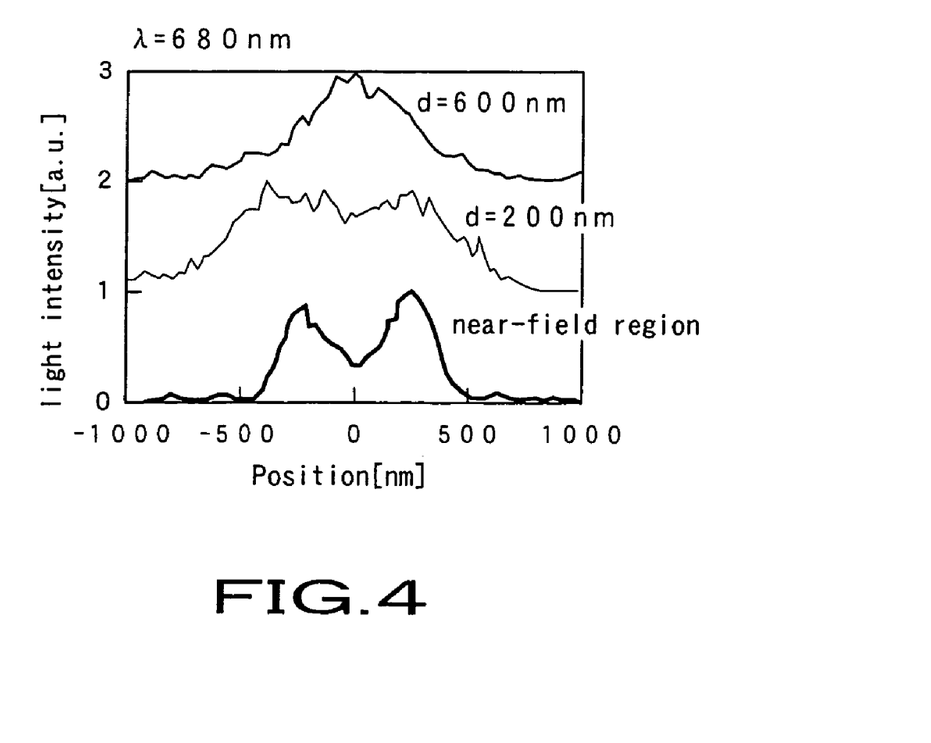
FIG. 4 is a graph showing the profile of light radiated from a light source in case the light has a wavelength ☐ of 680 nm.

FIG. 4 shows the profiles of light in case the wavelength of light λ radiated from the light source 11 is 680 nm. As may be seen from this FIG. 4, the profile of light, exhibiting twin peaks in the near-field region, undergoes transition to a single peak with increase in the distance d from the light radiating aperture D.

The reason the profile of light is changed in this manner may be such that the light shielding materials, used for the light shielding coating layer 33, such as Au, Ag or Al, differ in transmittance, from one wavelength to another, and such that the inter-mode interference is occurring within the core 31 of the optical probe 13.

Figure 5:
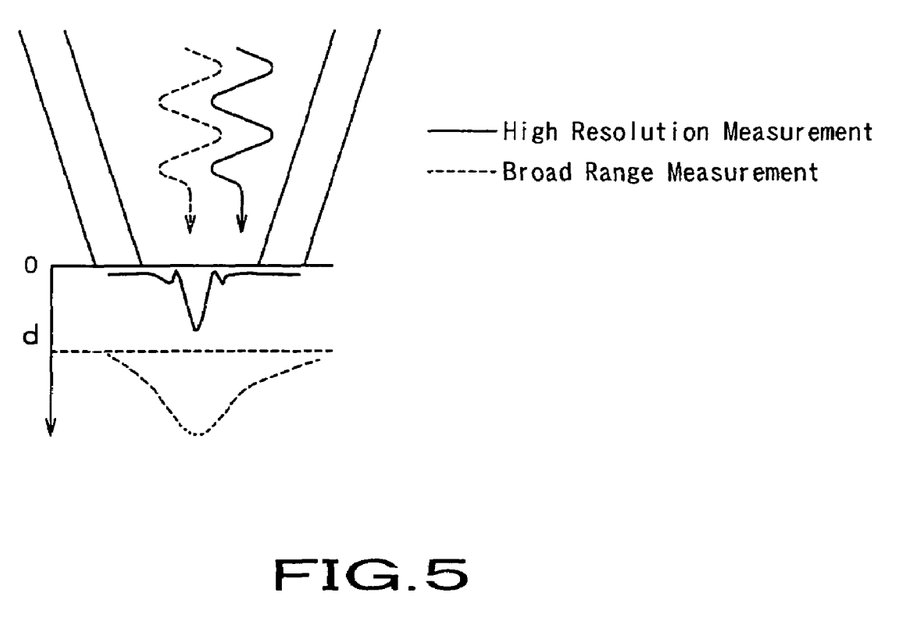
FIG. 5 is a schematic view for illustrating a case wherein the wavelength ☐ of light radiated from a light source is changed over from the one for broad range measurement to the one for high resolution measurement.

That is, with the light detecting apparatus 1, according to the present invention, the wavelength λ of light, radiated from the light source 11, is changed over from the one at the time of broad rage measurement to the one at the time of high resolution measurement, or vice versa, by the light wavelength converter 17, based on the above-mentioned wavelength-based difference of the light profile, as shown in FIG. 5. For example, the wavelength of light radiated from the light source 11 at the time of the high resolution measurement may be set to 830 nm, as shown in FIG. 5, whereby a profile of light sharpened at a center area may be formed in the near-field region, so that the near-field light may be allowed to seep efficiently via light radiating aperture D.

Furthermore, by setting the wavelength of light radiated from the light source 11 at the time of broad range measurement to 680 nm, the profile of light with a single peak and a large spot diameter may be formed at a distance d (=600 nm). This enables the light propagated through the core 31 to be illuminated efficiently on the surface for measurement 2a during the broad range measurement.

That is, with the light detecting apparatus 1 according to the present invention, a variety of measurements may be carried out by exploiting the wavelength dependency of the light profiles formed. Thus, by controlling the wavelength of light propagated through the core 31 in the sole as-assembled optical probe 13, a light spot by the near-field light or a light spot by the propagated light may efficiently be formed on the surface for measurement 2a, whereby the function of broad range measurement exploiting the propagated light and the function of high resolution measurement exploiting the near-field light may be efficiently implemented by the sole optical probe 13.

Moreover, with the present light detection apparatus 1, the diameter h of the light radiating aperture D in the optical probe 13 may be adjusted as necessary.

Figure 6:
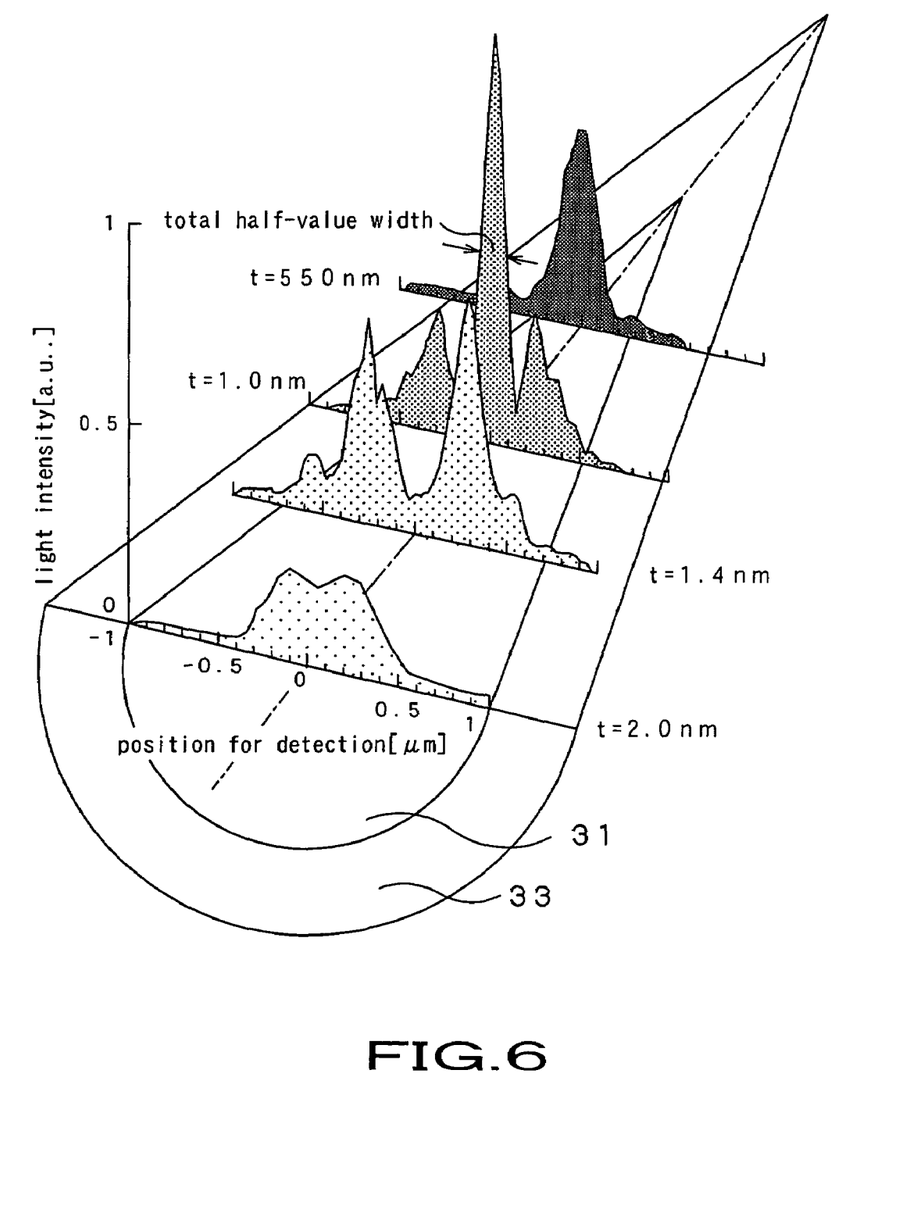
FIG. 6 illustrates the relationship between the profile of light and the diameter t of a light radiating aperture D.

FIG. 6 shows the relationship of the profile of light relative to the diameter t of the radiating aperture D. Referring to FIG. 6, the light profile, with the diameter t of the light radiating aperture D being 2.0 µm, has a peak centered about the detection position of 0 µm. In case the diameter t of the radiating aperture D is set to 1.4 µm, there are formed two peaks, on both sides of the detection position of 0 µm. The maximum value of the light intensity becomes larger than the one when the diameter t is 2.0 µm.

When the diameter t of the radiating aperture D is set to 1.0 µm, the light profile is such a one having a peak at the detection position of 0 µm and peaks at the detection positions of ±0.5 µm. With this light profile, the maximum value of the light intensity at the two peaks at the detection positions of ±0.5 µm is smaller than the maximum value of the light intensity at the detection position of 0 µm. By the way, the half-value width of the peak at the detection position of 0 µm is on the order of 150 nm. It is noted that, with the diameter t of the radiating aperture D of 550 nm, the light profile is such a one having a sole peak weaker than when the diameter t of the radiating aperture D is 1.0 µm.

Based on the relationship of the light profile, shown in FIG. 6, the diameter t may be optimized for the radiating aperture D of the optical probe 13 used for the light detecting apparatus 1. Moreover, by controlling the wavelength of light propagated through the core 31, with the dependency on the radiating aperture D in the light profile taken into consideration, it becomes possible to form a spot by the propagated light during the broad range measurement and a spot by the near-field light during the high resolution measurement on the surface for measurement 2a.

With the optical probe 13, used for the light detecting apparatus 1, it is possible to provide a radiating aperture having a diameter t not less than 0.9 µm. By so doing, most of the return light reflected on the surface for measurement 2a may be caused to fall on the radiating aperture D, so that, especially during broad range measurement when the distance h becomes longer, it becomes possible to suppress the volume of light received by the photodetector 14 from being lowered during broad rage measurement when the distance h becomes longer, thereby improving the S/N ratio of luminance signals obtained on opto-electric conversion.

In the foregoing, the light detection apparatus 1 of the present invention has been explained with reference to a case where the optical probe 13 provided with the radiating aperture D is mounted centrally of the protruded core 20a. However, the present invention is not limited to this particular configuration. For example, an optical probe 43 may also be used in which no light radiating aperture is provided by forming a light shielding coating layer 33a over the entire surface of the protruded core 20a, as shown for example in FIG. 7. In this configuration, the light propagated through the core 31 is transmitted through the light shielding coating layer 33a so as to be radiated towards the surface for measurement 2a, while the light incident from the surface for measurement 2a is transmitted through the light shielding coating layer 33a so as to be guided to the core 31.

Figure 7:
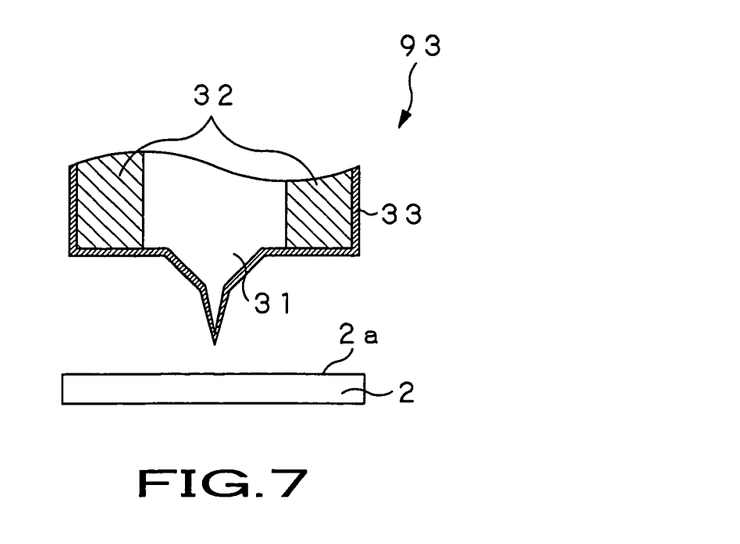
FIG. 7 is a schematic view for illustrating an optical probe not provided with the light radiating aperture.

Even with the optical probe 43, not having the light radiating aperture, the light shielding coating layer 33a, formed on the probe surface, resonates with the incident light to generate surface plasmon. This surface plasmon generates near-field light at the distal end of the probe to provide for high resolution measurement. The near-field light or the evanescent light, generated on the surface for measurement 2a, may be detected by the optical probe 43 for use in measurement operations.

In this case, the wavelength of light, for which the light shielding coating layer 33a exhibits high transmittance, or that for which the light shielding coating layer exhibits low transmittance, may be selected in dependence upon the subject for measurement, as the wavelength of light radiated from the light source. This provides for improved light utilization efficiency. As for the classification of the broad range measurement and the high resolution measurement, in case a probe having an aperture is used, measurement with the probe having the distance h (distance between the optical probe and the specimen) not less than the aperture diameter and measurement with the probe having the distance h less than the aperture diameter, may be classified as being the broad range measurement and the high resolution measurement, respectively. In case the probe used is not provided with an aperture, as shown in FIG. 7, measurement in which the distance h ☐ the radius of curvature at the distal end 20a of the core and that in which h<the radius of curvature at the distal end 20a of the core may be classified as being the broad range measurement and the high resolution measurement, respectively.

There is no particular limitation to the shape of the optical probes 13, 43 or to the material of the light shielding coating layer 33. That is, the shape or the material of the optical probes 13, 43 used may be determined in dependence upon the shape or the size of the spot to be formed on the surface for measurement 2a, as account is taken of the relationship with respect to the wavelength described above.

Figure 8:
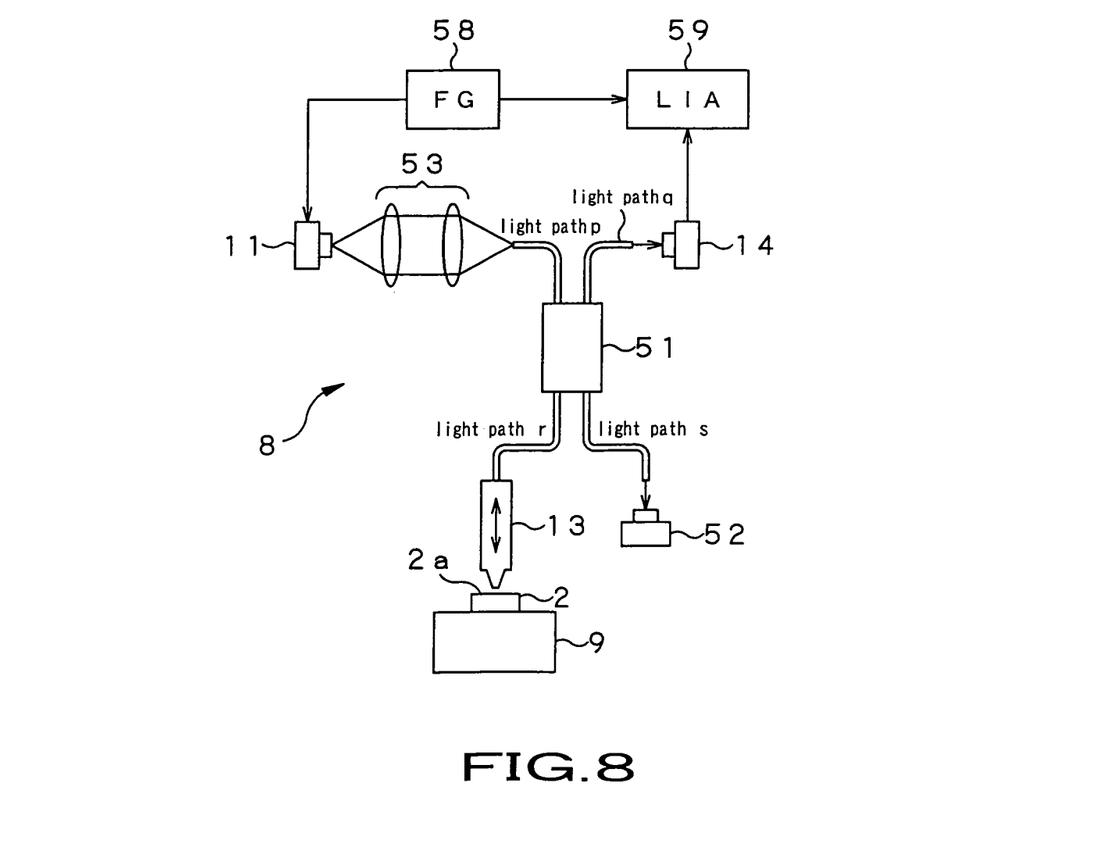
FIG. 8 is a schematic view showing another illustrative structure of a light detecting apparatus embodying the present invention.

The present invention is not limited to the light detecting apparatus 1 described above and may also be applied to a light detecting apparatus 8 shown for example in FIG. 8. In this light detecting apparatus 8, the same parts or components as those of the light detecting apparatus 1 are depicted by the same reference numerals, and the corresponding description is dispensed with.

This light detecting apparatus 8 includes a light source 11, radiating light, a light coupling optical system 53, controlling the spot diameter of light radiated from the light source 11, a fiber coupler 51 for branching the incident light, an optical probe 13 for collecting light from the fiber coupler 51 for illuminating the so collected light to the surface for measurement 2a of a specimen 2, a Z-axis stage 9 for causing movement of the optical probe 13 in a direction towards and away from the optical probe 13, a photodetector 14 for detecting return light from the surface for measurement 2a, and a monitor power meter 52 for monitoring the light branched by the fiber coupler.

The fiber coupler 51 operates for bifurcating the light radiated from the light source towards the optical probe 13 and towards the monitor power meter 52. In case of using a 2:2 fiber coupler for bifurcating the light in a 50%:50% ratio, the light incident from a light path p is radiated in the 50%:50% ratio on a light path r and on a light path s. The intensity of light radiated from the light path s is detected by the monitor power meter 52, and the distance between the light source 11 and the end face of the fiber coupler 51 connecting to the light path p is adjusted with the light intensity as detected as reference, in order to adjust the light guide efficiency. It is also possible to adjust and estimate the intensity of near-field light radiated from the optical probe 13.

After completion of the above adjustment, a spot by the near-field light seeping out is formed on the surface for measurement 2a, using the optical probe 13, as in the case of the photodetector 1. The return light from the surface for measurement 2a to the optical probe 13 is split, in a ratio of 50%:50%, in terms of light intensity, when passing through the fiber coupler 51, so that part of the return light is detected by the photodetector 14. This provides for measurement similar to that carried out by the light detecting apparatus 1.

With this light detecting apparatus 8, it is of course possible to apply frequency modulation to the light source 11, using a function generator (FG) 58, and to detect only the frequency component, using a lock-in amplifier (LIA) 59, to remove interference light.

Figure 9:
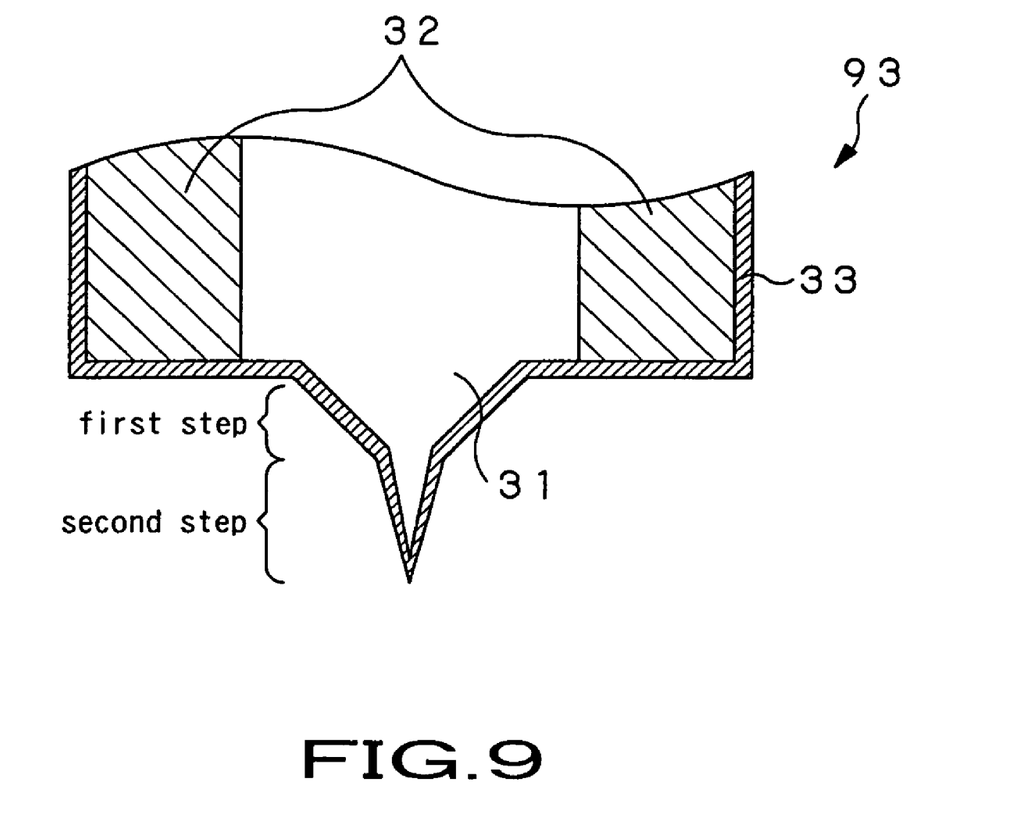
FIG. 9 is a schematic view for illustrating a modified optical probe mounted to a light detecting apparatus embodying the present invention.

The optical probe, arranged in the light detecting apparatus 1 of the present invention, is not limited to the above-described embodiment. For example, an optical probe 93, tapered in two steps, as shown in FIG. 9, may also be used. The parts or components of the optical probe 93 which are the same as those of the optical probe 13, are depicted by the same reference numerals, and the explanation here is dispensed with.

The optical probe 93 is formed of an optical fiber and is made up of a core 31 about which is provided a clad 32. The core 31 is finished to a dual step taper. The core 31 and the clad 32 are coated with a light shielding coating layer 33.

In case the light propagated through the core 31 is of a wavelength that may be transmitted through the light shielding coating layer 33, the propagated light, transmitted through the first step taper in FIG. 9, forms a spot on the surface for measurement 2a to provide for broad range measurement. If conversely the propagated light is of a wavelength that cannot be transmitted through the light shielding coating layer 33, the propagated light is collected by the first step taper to the second step taper to generate near-field light. The result is that the near-field light generating efficiency may be raised, while it becomes possible to provide for measurement to a higher resolution.

The optical probe 93 may be tapered in three or more steps for further raising the near-field light generating efficiency and for raising the ability for shear force resolution by sharpening.

With the apparatus and method for light detection, according to the present invention, in which light radiated from a core of an optical fiber probe, coated with a light shielding coating layer to provide a light radiating aperture, or from a core of an optical fiber probe, with the end of the core being coated with a light shielding coating layer, is propagated, and either the optical fiber probe is moved towards and away from the surface for measurement, or the surface for measurement is moved towards and away from the optical fiber probe, there is formed a spot of light, which is the light propagated through the core or the light seeping through the radiating aperture, on the surface for measurement, and the return light derived from the light spot is detected.

Thus, the measurement with the usual propagated light and that with the near-field light may selectively be realized, in a switching fashion, with the use of the sole as-assembled probe. The result is that an optical probe used only for broad range measurement need not be separately provided for a measurement system capable of realizing high resolution measurement employing near-field light, thus enabling the apparatus to be reduced in size to lower production cost. In addition, there is no necessity for exchanging an optical probe used, in switching from a broad range measurement to a high resolution measurement, thus relieving the user of excess load.

The present invention is not limited to the above embodiments explained with reference to the drawings and, as apparent to those skilled in the art, a variety of changes or substitutions by equivalents may be attempted without departing from the scope of the invention as defined in the appended claims.

INDUSTRIAL APPLICABILITY

With the a light detecting apparatus and method, according to the present invention, so far described in detail, in which a distal end of an optical fiber probe faces a surface for measurement, a spot of light from the optical fiber probe is formed on the surface for measurement, and light from the surface for measurement is detected by the optical fiber probe, there are provided a broad range measurement mode exploiting the light propagated through a core of the optical fiber probe, and a high resolution measurement mode exploiting near-field light seeping from the core of the optical fiber probe.

Hence, the measurement employing usual propagated light and measurement employing near-field light may be selectively realized in a switching fashion using the as-assembled sole optical probe. Consequently, there is no necessity of separately providing an optical probe, used solely for broad range measurement, in a measurement system for high resolution measurement employing near-field light, with the result that the apparatus may be reduced in scale, and hence the production cost may be diminished significantly. Moreover, there is no necessity for exchanging the optical probe to be in use, at the time of switching from the broad range measurement mode to the high resolution measurement mode, with the result that the user may be relieved of excessive labor.

The invention claimed is:

1. A light detecting apparatus comprising:
an optical fiber probe whose distal end faces a surface that it measures, the probe forming a spot of light on said surface, and detecting light from said surface for measurement; and
a probe controller that switches the light detecting apparatus between broad range measurement mode and high resolution measurement mode by controlling a distance between the distal end of said optical fiber probe and said surface for measurement based on said distance correlated to the value of the diameter of a light radiating aperture formed centrally of the distal end of a core of said optical fiber probe,
wherein said broad range measurement mode exploits the light propagated through said core of said optical fiber probe and said high resolution measurement mode exploits near-field light seeping from said core of said optical fiber probe.

2. The light detecting apparatus according to claim 1, wherein said probe controller switches to said broad range measurement mode by controlling said distance to exceed a preset value and to said high resolution measurement mode by controlling said distance to not exceed said preset value.

3. The light detecting apparatus according to claim 1, wherein a light radiating aperture is formed centrally of the distal end of said core.

4. The light detecting apparatus according to claim 1 wherein a light shielding coating layer is formed at the distal end of said core.

5. The light detecting apparatus according to claim 1 wherein said probe controller switches to said high resolution measurement mode after detecting the light from said surface by said broad range measurement mode.

6. The light detecting apparatus according to claim 1 further comprising:
   a light source radiating said propagated light; and
   a wavelength controller controlling the wavelength of the light radiated from said light source.

7. The light detecting apparatus according to claim 6, wherein said wavelength controller switches the wavelength of the light radiated from said light source between said broad range measurement mode and said high resolution measurement mode.

8. The light detecting apparatus according to claim 6, wherein
   said optical fiber probe has a light shielding coating layer in such a manner that a light radiating aperture is formed centrally of the distal end of said core, and
   said wavelength controller controls the wavelength of the light radiated from said light source to a wavelength determined based on the material of said light shielding coating layer.

9. The light detecting apparatus according to claim 6 further comprising a light monitor monitoring said propagated light radiated from said light source.

10. A light detecting method in which a distal end of an optical fiber probe faces a surface for measurement, the method comprising:
    forming a spot of light from said optical fiber probe on said surface for measurement;
    detecting light from said surface; and
    switching between broad range measurement mode and high resolution measurement mode by changing a distance between the distal end of said optical fiber probe and said surface, wherein
    the broad range measurement mode exploits the light propagated through a core of said optical fiber probe and the high resolution measurement mode exploits near-field light seeping from said core of said optical fiber probe.

11. The light detecting method according to claim 10 wherein switching is made to said broad range measurement mode when said distance exceeds a preset value and wherein switching is made to said high resolution measurement mode when said distance is not larger than said preset value.

12. The light detecting method according to claim 10 wherein switching is made between said broad range measurement mode and said high resolution measurement mode based on said distance correlated to the value of the diameter of a light radiating aperture formed centrally of the distal end of a core of said optical fiber probe.

13. The light detecting method according to claim 10 wherein the detecting the light from said surface includes forming a light radiating aperture centrally of the distal end of said core.

14. The light detecting method according to claim 10 wherein the detecting the light from said surface includes forming a light shielding coating layer in an optical fiber probe at the distal end of said core.

15. The light detecting method according to claim 10, wherein switching is made to said high resolution measurement mode after detecting the light from said surface by said broad range measurement mode.

16. The light detecting method according to claim 10 further comprising a light radiating step of radiating said propagated light and a wavelength controlling step of controlling the wavelength of light radiated from said light radiating step.

17. The light detecting method according to claim 16 wherein said wavelength controlling step includes switching the wavelength of light radiated in said light radiating step between said broad range measurement mode and said high resolution measurement mode.

18. The light detecting method according to claim 16 wherein
    the detecting the light from the surface includes said optical fiber probe having a light shielding coating layer forming a light radiating aperture, and
    in said wavelength controlling step, the wavelength of light radiated in said light radiating step is controlled to a wavelength determined based on the material of said light shielding coating layer.

19. The light detecting method according to claim 10 further comprising a light radiating step of radiating said propagated light and a light monitor step of monitoring the propagated light radiated in said light radiating step.

* * * * *